United States Patent [19]

Becker et al.

[11] 4,304,922
[45] Dec. 8, 1981

[54] PROCESS FOR THE PREPARATION OF URETHANE

[75] Inventors: Robert Becker; Johann Grolig, both of Leverkusen; Christian Rasp; Günter Stammann, both of Cologne, all of Fed. Rep. of Germany

[73] Assignee: Bayer Aktiengesellschaft, Leverkusen, Fed. Rep. of Germany

[21] Appl. No.: 125,395

[22] Filed: Feb. 27, 1980

[30] Foreign Application Priority Data

Mar. 2, 1979 [DE] Fed. Rep. of Germany ....... 2908252

[51] Int. Cl.$^3$ ............... C07C 125/065; C07C 125/073
[52] U.S. Cl. ..................................... 560/24; 560/25; 560/26; 560/28; 560/30; 560/31; 560/32; 560/33; 560/115; 560/132; 560/133; 560/134; 560/157; 560/158; 560/159; 560/161; 560/162; 560/163; 560/164
[58] Field of Search ..................... 560/24, 25, 22, 32, 560/30, 115, 132, 156, 157, 158, 26, 28, 31, 33, 133, 134, 159, 161, 162, 163, 164

[56] References Cited

U.S. PATENT DOCUMENTS

| | | | |
|---|---|---|---|
| 2,409,712 | 10/1946 | Schweitzer | 560/25 |
| 3,467,694 | 9/1969 | Hardy et al. | 560/24 |
| 3,627,813 | 12/1971 | Abbate et al. | 560/24 |
| 3,873,553 | 3/1975 | Hearsey | 560/25 |
| 4,134,880 | 1/1979 | Wiyata et al. | 560/24 |
| 4,178,455 | 12/1979 | Hirai et al. | 560/24 |

FOREIGN PATENT DOCUMENTS 1472243  5/1977  United Kingdom .

*Primary Examiner*—G. T. Breitenstein
*Attorney, Agent, or Firm*—Gene Harsh; Joseph C. Gil; Lyndanne M. Whalen

[57] ABSTRACT

Production of urethanes by the oxycarbonylation reaction of N,N'-disubstituted ureas and organic compounds containing at least one hydroxyl group with carbon monoxide in the presence of molecular oxygen and/or organic nitro compounds and a catalyst system comprising (a) a noble metal and/or noble metal compound of the eighth subgroup of the periodic system of elements and (b) a compound of an element and/or elements of the third to fifth main group and/or first to eighth subgroup of the periodic system of elements characterized in that said compounds are capable of undergoing Redox reactions under the reaction conditions.

13 Claims, No Drawings

PROCESS FOR THE PREPARATION OF URETHANE

FIELD OF THE INVENTION

This invention relates to an improved process for the preparation of urethane from N,N'-disubstituted ureas and organic compounds containing at least one hydroxyl group.

BACKGROUND OF THE INVENTION

Organic isocyanates are generally produced on a large commercial scale by the reaction of the corresponding amines with phosgene. Because of the toxicity of phosgene, considerable time has been spent trying to find a method of synthesis of organic isocyanates which would eliminate the need for phosgene. One such method consists of reacting organic nitro compounds with carbon monoxide and organic hydroxyl compounds to the corresponding urethanes and then decomposing these into isocyanates and compounds containing hydroxyl groups. This decomposition reaction can be preceded by a modification of the urethane obtained as intermediate product. Thus, for example, the urethane obtainable from nitrobenzene, carbon monoxide and ethanol could first be reacted with formaldehyde to form the bisurethane of 4,4'-diisocyanatodiphenyl methane, which could then be converted into 4,4'-diisocyanatodiphenyl methane with elimination of the ethanol.

The decomposition of urethanes into the corresponding isocyanates and hydroxyl compounds has been described, for example, in German Offenlegungsschrift No. 2,421,503 and the prior publication cited therein.

Methods for the preparation of urethanes described in the patent literature include the reaction of nitro compounds with carbon monoxide and alcohols in the presence of selenium or selenium compounds (German Offenlegungsschriften No. 2,343,826 (U.S. Pat. No. 3,895,054): 2,614,101 and 2,623,694 (U.S. Pat. No. 4,080,365) or of noble metals, in particular palladium, in the presence of Lewis acids (German Offenlegungsschriften Nos. 1,568,044 and 2,603,574).

For the preparation of a mononitro compound, this reaction proceeds in accordance with the following stoichiometric equation:

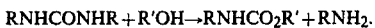

$$R-NO_2 + 3CO + R'OH \rightarrow RNHCO_2R' + 2CO_2.$$

The general reaction equation is as follows:

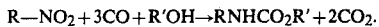

$$R(NO_2)_x + 3xCO + xR'OH \rightarrow R(NHCO_2R')_x + 2xCO_2.$$

This means that for each mol of urethane group to be produced three mols of carbon monoxide are used up and two mols of carbon dioxide are formed. Only one-third of the carbon monoxide put into the process is used for the formation of urethane groups. Two-thirds are converted into the technically useless inert carbon dioxide. Large amounts of heat are evolved in the exothermic formation of carbon dioxide. Therefore, expensive equipment for removing the heat of reaction is necessary in the known industrial method of synthesizing a urethane from a nitro compound, carbon monoxide and alcohol.

The patent literature also teaches how to react N,N'-dialkyl ureas or N,N'-diaryl ureas with alcohols to produce a urethane and an amine, for example, U.S. Pat. No. 2,409,712. The following represents this reaction scheme:

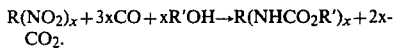

$$RNHCONHR + R'OH \rightarrow RNHCO_2R' + RNH_2.$$

In this method, however, only one-half of the alkyl or aryl groups in the urea is converted into urethane while the other half is converted to the free amine.

DESCRIPTION OF THE INVENTION

It has now been found that N,N'-disubstituted ureas can be reacted with organic compounds containing at least one hydroxyl group to produce urethanes without free amine being split off in the process. The yield, based on N,N'-disubstituted urea, is therefore virtually doubled. This is accomplished where ureas together with organic compounds containing at least one hydroxyl group are subject to an oxycarbonylation with carbon monoxide under specific reaction conditions.

The present invention thus relates to a process for the preparation of urethanes comprising reacting N,N'-disubstituted ureas and organic compounds having at least one hydroxyl group, characterized in that these starting compounds are subjected to an oxycarbonylation in the presence of carbon monoxide and molecular oxygen and/or organic nitro compounds as oxidizing agent and a catalyst comprising:

(a) a noble metal and/or a noble metal compound of the eighth sub-group of the periodic system of elements and (b) a compound of elements of the third to fifth main group and/or first to eighth subgroup of the periodic system of elements, other than the compounds of group (a) which compound is capable of undergoing Redox reactions under the reaction conditions.

The N,N'-disubstituted ureas suitable as starting materials for the instant process may be any ureas of this type which are substituted with an organic group. They may also contain nitro groups in which case the addition of other nitro compounds may be omitted. They generally have a molecular weight of from 88 to 500, preferably from 212 to 330. The starting materials also include any organic compounds containing at least one hydroxyl group, for example, substituted aliphatic, cycloaliphatic and/or aromatic monohydroxyl or polyhydroxyl compounds. These compounds generally have a molecular weight in the range of from 32 to 300, preferably from 32 to 102.

The organic substituents on the N,N'-disubstituted ureas may be the same or different. They may be aliphatic, cycloaliphatic or aromatic groups. Examples of these groups are methyl; ethyl; ethylene; propyl; isopropyl; 1,2-propylene; 1,3-propylene; butyl; isobutyl; sec.-butyl and tert.-butyl groups.

Further examples of suitable groups are the pentyl; hexyl; heptyl; octyl; decyl; dodecyl; cetyl; cyclopentyl; cyclohexyl; phenyl; p-tolyl; o-tolyl; m-tolyl; o-chlorophenyl; p-chlorophenyl; m-chlorophenyl; o-aminophenyl; p-aminophenyl; m-aminophenyl; o-nitrophenyl; p-nitrophenyl and m-nitrophenyl groups. 3-amino-2-methyl phenyl; 3-amino-4-methyl phenyl; 5-amino-2-methyl phenyl; 3-nitro-2-methyl phenyl; 3-nitro-4-methyl phenyl; 5-nitro-2-methyl phenyl; 1-naphthyl; 2-naphthyl; 6-amino-1-naphthyl and 6-nitro-1-naphthyl are also suitable groups.

N,N'-disubstituted ureas containing aromatic groups are preferred. Examples of these preferred ureas are N,N'-diaryl ureas. Specific suitable examples are N,N'-diphenyl urea, N,N'-di-(p-tolyl)-urea; N,N'-di-(o-tolyl)-urea; N,N'-di-(o-aminophenyl)-urea; N,N'-di-(p-aminophenyl)-urea; N,N'-di-(o-nitrophenyl)-urea; N,N'-di-(3-amino-2-methyl phenyl)-urea; N,N'-di-(3-amino-4-methyl phenyl)-urea; N,N'-di-(5-amino-2-methyl phenyl)-urea; N,N'-di-(3-nitro-4-methyl phenyl)-urea; N,N'-di-(5-nitro-2-methyl phenyl)-urea and N,N'-di-(3-nitro-2-methyl phenyl)-urea. N-(3-amino-2-methyl phenyl)-N'-(3-nitro-2-methyl phenyl)-urea; N-(3-amino-4-methyl phenyl)-N'-(3-nitro-4-methyl phenyl)-urea; N-(5-amino-2-methyl phenyl)-N'-(5-nitro-2-methyl phenyl)-urea; N-(3-amino-2-methyl phenyl)-N'-(5-amino-2-methyl phenyl)-urea; N-(3-amino-2-methyl phenyl)-N'-(3-amino-4-methyl phenyl)-urea; N-(3-amino-4-methyl phenyl)-N'-(5-amino-2-methyl phenyl)-urea; N-(3-nitro-2-methyl phenyl)-N'-(5-amino-2-methyl phenyl)-urea; N-(3-nitro-2-methyl phenyl)-N'-(5-nitro-2-methyl phenyl)-urea are also examples of specifically suitable N,N'-diaryl ureas. The following are particularly preferred; N,N'-diphenyl urea; N,N'-di-(p-tolyl)-urea; N,N'-di-(o-tolyl)-urea; N,N'-di-(3-amino-2-methyl phenyl)-urea; N,N'-di-(3-amino-4-methyl phenyl)-urea; and N,N'-di-(5-amino-2-methyl phenyl)-urea. Also preferred are the corresponding asymmetric N,N'-disubstituted diaryl ureas which are amino or methyl substituted on the aromatic rings, and any mixtures of these compounds.

The starting materials for the instant process also includes any organic compounds containing hydroxyl groups. Examples are any monohydric or polyhydric alcohols or monovalent or polyvalent phenols. Suitable alcohols include, for example, those having a molecular weight in the range of 32 to 300. These may include linear or branched chain monohydric or polyhydric alkanols or alkenols as well as any monohydric or polyhydric cycloalkanols, cycloalkenols or aralkyl alcohols.

The alcohols may also carry any inert substituents such as, for example, halogen atoms, sulphoxide groups, sulphone groups, carbonyl groups or carboxylic acid ester groups. Alcohols having ether bridges are also suitable in principle. The following are examples of suitable alcohols: methanol, ethanol, n-propanol, isopropanol, n-butanol, n-pentanol, n-hexanol, cyclohexanol, benzyl alcohol, chloroethanol, ethylene glycol, diethylene glycol, propylene glycol, dipropylene glycol, glycerol, hexane-triol and trimethylol propane. Monohydric aliphatic alcohols having 1 to 6 carbon atoms are preferably used.

Suitable phenols include, in particular, those within a molecular weight range of 94 to 300. Examples are phenol, the isomeric chlorophenols, cresols, ethyl phenols, propyl phenols, butyl phenols or higher alkyl phenols. Pyrocatechol, 4,4'-dihydroxy-diphenyl methane, bisphenol-A, anthranol, penanthranol, pyrogallol or phloroglucinol are also suitable. The alcohols exemplified above are preferred over the exemplified phenols. Ethanol is the particularly preferred hydroxyl compound to be used in the instant process.

The organic hydroxyl compounds are generally used in such quantities, in the instant process, that the reaction mixture contains from 1 to 100 hydroxyl groups for each urethane group to be formed. When calculating the quantity of hydroxyl compound required, it should be taken into account that when amino substituted ureas are used or when nitro compounds are present in the reaction mixture, the amino and nitro groups are also converted into urethane groups. That is, one equivalent of hydroxyl groups is required for each mol of urea as well as for each mol of amino or nitro groups in the stoichiometric reaction.

Carbon monoxide is used as the other reactant in the instant process. This starting material is generally used in a quantity corresponding to 1 to 30 mol per mol of urethane to be produced. When calculating this quantity, the fact that, in the stoichiometric reaction, 1 mol of carbon monoxide is required for each mol of urea and each mol of amino or nitro groups present in the reaction mixture must be taken into account.

The reaction according to the instant invention is carried out in the presence of oxidizing agents and catalysts.

The oxidizing agent used may be molecular oxygen in the pure form or in the form of mixtures with inert gases such as nitrogen or carbon dioxide, in particular in the form of air. In the presence of molecular oxygen, oxycarbonylation proceeds in accordance with the following reaction equation:

$$R^1NHCONHR^2 + (\tfrac{1}{2})O_2 + CO + 2R'OH \rightarrow R^1NHCO_2R' + R^2NHCO_2R' = H_2O$$

wherein $R^1$ may be different from $R^2$, but $R^1$ and $R^2$ are preferably the same.

Organic nitro compounds are the preferred oxidizing agents. Any of a wide variety of nitro compounds may be used. Under the conditions of oxycarbonylation, these are also converted into urethanes, for example, according to the following reaction equation:

$$2R^2NHCONHR^2 + R^3NO_2 + 3CO + 5R'OH \rightarrow 2R^1NHCO_2R' + 2R^2NHCO_2R' + R^3NHCO_2R' + 2H_2O.$$

It is particularly preferred to carry out the reaction of symmetric N,N'-diaryl ureas in the presence of an aromatic nitro compound in which the aryl group is the same as the aryl groups of the urea. Oxycarbonylation then proceeds in accordance with the following equation to form a single urethane:

$$2RNHCONHR + RNO_2 + 3CO + 5R'OH \rightarrow 5RNHCO_2R' + 2H_2O.$$

To realize optimum yield when using organic nitro compounds as the sole oxidizing agents, the quantities of urea compound and nitro compound are preferably calculated to provide two mols of urea for each mol of nitro groups in the reaction mixture. When amine substituted ureas are used, however, it must be remembered that an additional half mol of nitro groups is necessary for each mol of amino groups in order to convert the amino groups into urethane groups. When nitro substituted ureas are used, it is of course necessary to provide an additional oxidizing agent, provided the quantity of nitro groups present is sufficient for the stoichiometric conversion to urethane.

To realize optimum yields when molecular oxygen is used as the sole oxidizing agent in the above reaction equation, at least one half mol of oxygen must be present for each mol of urea. If amino groups are present, at least one half mol of oxygen must also be available for each mol of amino groups. The oxygen may be used in excess. Less than equivalent quantities of oxygen would reduce the yield. It is advantageous to add an inert gas such as nitrogen or carbon dioxide in such quantities that the reaction can be carried out without the risk of explosion of the mixtures of oxygen and carbon monoxide or mixtures of oxygen and alcohol. If no inert gas is added, the quantity of oxygen used should be calculated to avoid the formation of explosive mixtures with carbon monoxide and the alcohol component. Molecular oxygen is preferably used in the form of air or of mixtures of air and nitrogen.

Oxygen and a nitro compound may be used together as oxidizing agents in which case the nitro compound may be used in less than the stoichiometric quantity. The oxidizing agents may be added in excess so that when nitro compounds are used they may be added in quantities providing a molar ratio of urea to nitro groups ranging from 1:1 to 4:1, in particular from 1.5:1 to 2.5:1 and most preferably from 1.8:1 to 2.2:1.

The nitro compounds used for the instant process may be any organic compounds, generally with molecular weights from 61 to 400, preferably from 123 to 262, having at least one aliphatically, cycloaliphatically and/or aromatically bound nitro group.

The following are examples of suitable aromatic nitro compounds: nitrobenzene; o-dinitrobenzene; m-dinitrobenzene; p-dinitrobenzene; o-chloro-nitrobenzene; m-chloro-nitrobenzene; o-chloro-nitrobenzene; o-nitrotoluene; m-nitrotoluene and p-nitrotoluene. Also suitable are o-amino-nitrobenzene; m-amino-nitrobenzene; p-amino-nitrobenzene; 2-amino-3-nitrotoluene; 3-amino-2-nitrotoluene; 2-amino-4-nitrotoluene; 4-amino-2-nitrotoluene; 2-amino-5-nitrotoluene; 2-amino-6-nitrotoluene; 5-amino-2-nitrotoluene; 3-amino-4-nitrotoluene; 4-amino-3-nitrotoluene; 3-amino-4-nitrotoluene and 3-amino-5-nitrotoluene. 2,3-dinitrotoluene; 2,4-dinitrotoluene; 2,5-dinitrotoluene; 2,6-dinitrotoluene; 3,4-dinitrotoluene; 3-nitro-o-xylene; 4-nitro-o-xylene; 2-nitro-m-xylene; 5-nitro-m-xylene; nitro-p-xylene; 3,4-dinitro-o-xylene; 3,5-dinitro-o-xylene; 3,6-dinitro-o-xylene; 4,5-dinitro-o-xylene; 2,4-dinitro-m-xylene; 2,5-dinitro-m-xylene; 4,5-dinitro-m-xylene; 4,6-dinitro-m-xylene; 2,3-dinitro-p-xylene; 2,6-dinitro-p-xylene are also suitable compounds. Still more examples of suitable compounds are 1-nitronaphthalene; 2-nitronaphthalene; dinitronaphthalenes; nitroanthracenes; nitro-diphenyls; bis-(nitrophenyl)methanes; bis-(nitrophenyl)-thio-ethers; bis-(nitrophenyl)-sulphones; nitrodiphenoxy alkanes and nitrophenothiazines.

The following are suitable cycloaliphatic nitro compounds: nitrocyclobutane; nitrocyclopentane; nitrocyclohexane; 1,2-dinitro cyclohexane; 1,3-dinitro cyclohexane; 1,4-dinitro cyclohexane and bis-(nitrocyclohexyl)-methanes.

The following are examples of suitable nitro alkanes: nitromethane, nitroethane, 1-nitropropane; 2-nitropropane; nitrobutanes; nitropentanes; nitrohexanes; nitrodecanes nitrocetanes; 1,2-dinitroethane, 1,2-dinitropropane; 1,3-dinitropropane; dinitrobutanes; dinitropentanes; dinitrohexanes; dinitrodecanes; phenylnitromethane; bis-(nitromethyl)-cyclohexanes; bis-(nitromethyl)-benzenes and ω-nitro carboxylic acid nitriles.

Aromatic nitro compounds of the type exemplified above are preferred for the instant process. The following are particularly preferred: nitrobenzene; 1,3-dinitrobenzene; 2,4-dinitrobenzene; 2,6-dinitrotoluene and 1,5-dinitronaphthalene.

The catalyst systems used for the instant process comprise: (a) noble metals of the eighth subgroup of the periodic system as their main constituent and (b) a cocatalyst component.

Components (a) are either free noble metals of the eighth subgroup of the periodic system or compounds of these metals soluble in the reaction mixture. The noble metals are most preferably added as compounds which are soluble in the reaction mixture, for example, as chlorides, bromides, iodides, chloro complexes, bromo complexes, iodo complexes, acetates, acetyl acetonates and other soluble noble metal compounds. Suitable noble metals include Ru, Rh, Pd, Os, Ir and Pt. The preferred noble metals are palladium and rhodium, palladium being particularly preferred. Especially particularly preferred is palladium in the form of soluble palladium chloride. The preferred concentrations, based on the reaction mixture including any solvent added, are generally in the range of 0.0001 to 0.1% by weight, in particular 0.001 to 0.01% by weight, calculated as noble metal. If lower concentrations of noble metal are used, the reaction speed is too slow. Although higher noble metal concentrations could be used, this is uneconomical owing to the possible loss of noble metal, especially since any further increase in concentration does not increase the urethane yield.

The cocatalysts (b) may be any compounds capable of Redox reactions under the reaction conditions of elements from the third to fifth main and first to eighth subgroup of the periodic system other than the compounds of group (a). The compounds of these metals are preferably their chlorides, oxychlorides, oxides and/or hydroxides. If oxides or hydroxides are used, certain activating chlorides are preferably also added.

The following are examples of suitable cocatalysts: copper(II)chloride; thallium(III)chloride; tin(II)chloride; tin(IV)chloride; arsenic(III)chloride; bismuth(III)chloride; vanadium(III)chloride; chromium(III)chloride; molybdenum(IV)chloride; tungsten(V)chloride; tungsten(VI)chloride; manganese(II)chloride; iron(II)chloride; iron(III)chloride; iron oxychloride; cobalt(II)chloride; copper(II)oxide; copper(II)hydroxide; thallium(I)hydroxide; tin(II)oxide; tin(II)hydroxide; vanadium pentoxide; molybdenum trioxide; tungsten trioxide; manganese dioxide; iron(II)oxide; iron(II)hydroxide and iron(III)hydroxide. Also suitable are the iron(III)oxides, such as, for example, $\alpha$-$Fe_2O_3$ or $\gamma$-$Fe_2O_3$; hydrated iron(III)oxides such as, for example, $\alpha$-FeO-OH; $\beta$-FeO-OH or $\gamma$-FeO-OH and iron spinel $Fe_3O_4$.

The particularly preferred cocatalysts include iron(II)chloride, iron(III)chloride, iron oxychloride and the oxides and hydrated oxides of trivalent iron.

The oxides or hydroxides exemplified above are often completely inert under the reaction conditions. It is necessary in these cases, therefore, to use activating chlorides. These activating chlorides are compounds which contain anionically bound chlorine in the form of chloride and which are capable of reacting under the reaction conditions with the exemplified oxides or hydroxides to convert them at least partly into the corresponding chlorides or oxychlorides. Suitable activating chlorides include, for example, the hydrochlorides of tertiary amines with molecular weights ranging from 59 to 300. Hydrochlorides of primary amines in which the substituents are preferably the same as the substituents of the ureas used, for example, aniline hydrochloride when diphenyl urea is used are also suitable. Hydrogen chloride, iron(II)chloride and iron(II)chloride complexes are more examples of suitable chloride compounds. The following are particularly suitable: pyridine hydrochloride; aniline hydrochloride, the hydrochloride of 2,4-diamino toluene, hydrogen chloride, iron(II)chloride and complexes of iron(II)chloride. Combinations of the last mentioned compounds are particularly preferred. Activating chlorides with oxides and hydrated oxides of trivalent iron are particularly valuable cocatalysts.

The concentrations at which the cocatalysts including the activating chlorides are used in the instant process are generally from 0.1 to 20% by weight, preferably from 1 to 5% by weight, based on the reaction mixture including any solvents used. If any activating chlorides are required, they are generally used in proportions of 0.05 to 10% by weight, preferably from 0.1 to 2.5% by weight.

The reaction may be carried out in the presence or absence of a solvent. The organic hydroxyl compound preferably used in excess generally serves as solvent. Inert solvents may also be added in quantities of up to 80% by weight based on the whole reaction mixture. Regardless of whether the solvent used is a hydroxyl compound used in excess or an inert solvent, its quantity must be such that the heat of reaction of exothermic urethane formation can be removed without any undue rise in temperature. The instant process is, therefore, generally carried out using a concentration of urea compounds of from 5 to 50% by weight, preferably from 5 to 20% by weight, and organic nitro compounds as oxidizing agents at a concentration of from 1 to 20% by weight, preferably from 5 to 10% by weight, based on the whole reaction mixture including the solvent.

The solvents used should be inert towards the reactants and the catalyst system. Examples are aromatic, cycloaliphatic and aliphatic hydrocarbons which may be substituted by halogen, such as benzene, toluene, xylene, chlorobenzene, dichlorobenzene, trichlorobenzene, chloro-naphthalene, cyclohexane, methyl cyclohexane, chloro-cyclohexane, methylene chloride, carbon tetrachloride, tetrachloroethane, trichlorotrifluoroethane and similar compounds.

The reaction temperature generally ranges from 100° C. to about 300° C., in particular from 130° C. to 250° C. and most preferably from 140° C. to 220° C. The pressure must be calculated to ensure the continuous presence of a liquid phase and is generally in the range of 5 to 500 bar, most preferably from 30 to 300 bar at the reaction temperature. The reaction time required for quantitative conversion varies from a few minutes to several hours, according to the primary amine and hydroxyl compound used and any organic nitro compound present.

The reaction of the ureas with hydroxyl compounds, carbon monoxide and oxidizing agent to form urethanes may be carried out batchwise or continuously.

The batchwise reaction may be carried out in a high pressure autoclave with small quantities of homogeneously dissolved noble metal and a sufficient excess of catalyst, and in the presence of an activating chloride, if necessary. Compounds which are insoluble in the reaction medium, such as iron oxides or hydrated iron oxides, may be added in the form of a fine powder. The activating additives may be added in the form of a homogeneous alcoholic solution. Undissolved excess cocatalyst components may be distributed by vigorous stirring of the reaction mixture or circulation by pumps. The exothermic heat of reaction may be removed by internally installed cooling apparatus or, if the reaction mixture is circulated by pumps, it may be removed by an external heat exchanger. Working up of the reaction product and return of the catalyst may be carried out by various methods, according to the solubility of the resulting urethane in the reaction mixture. If the urethanes are readily soluble, for example, the major portion of the cocatalyst mixture which is only sparingly soluble at low temperatures may be removed from the reaction product together with the major portion of absorbed palladium and organic amine salt, for example, by filtration or centrifuging. These compounds may be used again for a fresh reaction of primary amines with hydroxyl compounds, carbon monoxide and oxidizing agent. The liquid reaction mixture may be separated into solvents, pure urethanes and small quantities of by-products, if any, by the usual methods, e.g. by fractional distillation, either intermittently or continuously. The distillation residue contains small quantities of cocatalyst constituents dissolved in the reaction mixture and/or traces of noble metal and/or noble metal compounds. These substances may be returned for use in a fresh reaction.

If the urethanes are only soluble in the solvent or in excess hydroxyl compound, a modified method may be employed for working up the reaction mixture. For example, after release of pressure, the major portion of catalyst may be removed by filtration or centrifuging at a pressure and elevated temperature at which the urethanes are still dissolved but most of the catalyst system of noble metal/cocatalyst mixture precipitates. The sparingly soluble urethane, possibly together with small quantities of sparingly soluble by-products and residues of catalyst, may then be crystallized by lowering the temperature. The mother liquor, which still contains small quantities of by-products, dissolved urethane and possibly dissolved cocatalyst constituents in addition to the solvent or excess organic hydroxyl compound used as solvent, may then either be directly returned to the reaction vessel, or the low boiling by-products contained in it may first be removed, for example, by distillation. Higher boiling by-products which cannot be removed by crystallization may be removed continuously from the return stream as the distillation residue obtained from distilling an aliquot portion of the mother liquor. The crude urethane precipitated may be recrystallized, for example, by crystallization from a solvent which dissolves the urethane at elevated temperatures but not the by-products and catalyst residues. Examples of such solvents include isooctane, benzene, toluene, xylene, chloro-benzene and dichlorobenzene. Those residues which are insoluble at elevated temperatures may be converted by oxidation into insoluble oxides such as, for example, iron oxides and an exhaust gas resulting from the organic impurities, which gas consists mainly of carbon dioxide, oxygen, nitrogen and possibly readily volatile organic impurities. The exhaust gas may, depending on its composition, either be directly discharged into the atmosphere or subjected to a catalytic afterburning to remove remaining impurities by oxidation. The oxidic compound obtained from the residue, which compound may still contain small quantities of noble metal and/or noble metal compound, is returned to the oxycarbonylation process.

The reaction gas obtained from oxycarbonylation may contain unreacted carbon monoxide, low boiling organic constituents, small quantities of carbon dioxide and also, if molecular oxygen was used as oxidizing agent, small quantities of unreacted oxygen, as well as the inert gas introduced, such as nitrogen. This reaction gas may be readjusted to the reaction pressure after removal of the low boiling organic by-products and possibly carbon dioxide. It may then be returned to the reaction with replacement of the quantities of carbon monoxide and, if indicated, molecular oxygen which have been used up.

The continuous reaction may be carried out in a cascade of reaction vessels, a system of reaction pipes, several reaction coils arranged one behind the other, an adiabatic reaction tube or several such tubes arranged one behind the other, or a bubble column. The heat may be removed either internally, for example, by the installation of cooling assemblies, or externally through a system of heat exchanger pipes, or adiabatically by the thermal capacity of the reaction mixture, followed by cooling in external cooling apparatus.

Subsequent working up may be carried out as described above, either continuously or discontinuously.

If the products of the instant process are used for their preferred purpose as intermediate products for the preparation of the corresponding isocyanates, it is often unnecessary to prepare them in the pure state and it may be sufficient to use the crude products obtained after filtering off the catalyst and, if indicated, distilling off the solvent.

The following examples serve to illustrate the process of the invention without restricting it in any way. In the Examples, all quantities quoted represent parts by weight or percent by weight, unless otherwise indicated.

EXAMPLES

EXAMPLE 1

250 g of a reaction mixture of the following composition were introduced into a 0.7 liter autoclave: $2\times10^{-3}\%$ by weight of palladium chloride, 3.7% by weight of iron oxychloride, 18.5% by weight of N,N'-diphenyl urea and 77.8% by weight of ethanol. 100 bar of carbon monoxide and 20 bar of air were forced in at room temperature. The mixture was allowed to react for one hour at 180° C. Gas chromatographic analysis of the liquid reaction product revealed 98% conversion of the diphenyl urea introduced into the process and a phenyl urethane selectivity of 72%, based on diphenyl urea, and of 98%, based on the reacted ethanol.

EXAMPLE 2

The same reaction mixture was used as in Example 1 but reacted twice, each time with 100 bar of carbon monoxide and 20 bar of air for one hour, so that the total reaction time was two hours at 180° C. The diphenyl urea conversion was 99% and the phenyl urethane selectivities were: 88% based on diphenyl urea and 98% based on ethanol.

EXAMPLE 3

The procedure was the same as in Example 1. A mixture of $\alpha$-$Fe_2O_3$ (2.4% by weight) and aniline hydrochloride (3% by weight) was used as cocatalyst. Diphenyl urea conversion was quantitative and 80 mol % of phenyl urethane, based on diphenyl urea, and 98 mol % thereof, based on reacted ethanol, were obtained.

EXAMPLES 4 TO 8

The following table gives the results of the reactions obtained when various cocatalysts based on oxide and activating chloride were used. 250 g of a mixture of the following composition were used in each case in a 0.7 liter autoclave: $1.7\times10^{-3}\%$ by weight of $PdCl_2$, 2.4% by weight of an oxide capable of a Redox reaction, 3% by weight of aniline hydrochloride, 13.5% by weight of N,N'-diphenyl urea and 81.1% by weight of ethanol. In each experiment, the mixture was reacted three times with 100 bar of carbon monoxide and 20 bar of air (at room temperature), each time for one hour at 180° C. (total reaction time-3 hours at 180° C. in each experiment). The results shown in the following table were obtained:

| Example Number | Cocatalyst Oxide | Diphenyl Urea Conversion % | Phenyl Urethane Selectivity | |
|---|---|---|---|---|
| | | | Urea | Ethanol |
| 4 | $V_2O_5$ | 99 | 93 | 84.4 |
| 5 | $MnO_2$ | 100 | 90 | 99.3 |
| 6 | $MoO_3$ | 100 | 85 | 77 |
| 7 | $WO_3$ | 99 | 82.4 | 94.1 |
| 8 | $Sb_2O_3$ | 99.5 | 94 | 87.4 |

EXAMPLE 9

250 g of a reaction mixture of the following composition were introduced into a 0.7 liter refined steel autoclave: $2\times10^{-3}$ by weight of $PdCl_2$, 4% by weight of iron oxychloride, 20% by weight of a mixture of N,N'-diphenyl urea and nitrobenzene in a molar ratio of diphenyl urea/nitrobenzene=2:1 and 76% by weight of ethanol. 120 bar of monoxide were forced in at room temperature and the mixture was reacted for one hour at 160° C. Gas chromatographic analysis showed quantitative conversion of the diphenyl urea and the formation of phenyl urethane with a selectivity of 96%, based on diphenyl urea and nitrobenzene, and of 93% based on ethanol.

EXAMPLES 10 TO 14

The following Examples illustrate the influence of other noble metals on oxycarbonylation of N,N'-diphenyl urea (DPH) with nitrobenzene (NB):

| Conditions: | |
|---|---|
| Cocatalyst | 3.7% by weight of iron oxychloride |
| Diphenyl urea: | 14.93% by weight |
| Nitrobenzene: | 4.33% by weight |
| Molar ratio of diphenyl urea to nitrobenzene: | 2:1 |
| Alcohol: | 77% by weight of ethanol |
| Carbon monoxide pressure: | 120 bar at 20° C. |
| Quantity of reaction mixture used: | 270 g (in 0.7 liter refined steel autoclave) |

Results:

| Example Number | Noble Metal Compound (% by weight) | Temperature °C. | Time Hrs. | Conversion % | |
|---|---|---|---|---|---|
| | | | | DPH | NB |
| 10 | $RhCl_3 (2.7\times10^{-3})$ | 150 | 2 | 89 | 100 |
| 11 | $RhCl_3 (2.7\times10^{-3})$ | 180 | 1 | 99 | 100 |
| 12 | $IrCl_3 (3.7\times10^{-3})$ | 180 | 1 | 99 | 100 |
| 13 | $PtCl_4 (3.7\times10^{-3})$ | 180 | 2 | 99 | 100 |
| 14 | $RuCl_3 (3.7\times10^{-3})$ | 180 | 2 | 99 | 100 |

| Example Number | Phenyl Urethane Selectivity % | |
|---|---|---|
| | Based on DPH + NB | Ethanol |
| 10 | 95 | 100 |
| 11 | 99 | 98 |
| 12 | 90 | 98 |
| 13 | 93 | 94 |

| | | |
|---|---|---|
| -continued | | |
| 14 | 88 | 98 |

EXAMPLES 15 TO 22

The following Examples illustrate the influence of the cocatalyst on oxycarboxylation of N,N'-diphenyl urea (DPH) with nitrobenzene (NB).

| Conditions: | |
|---|---|
| Noble metal: | $1.8 \times 10^{-3}\%$ by weight of $PdCl_2$ |
| DPH + NB: | 20% by weight (in ethanol) |
| Molar ratio $\frac{DPH}{NB}$ = | 1.5:1 |
| CO pressure: | 120 bar at 20° C. |
| Temperature: | 180° C. |
| Reaction time: | 1 h |
| Reaction mixture: | 270 g (in 0.7 liter refined steel autoclave) |

Results:

| Example Number | Cocatalyst (% by weight) | Conversion % | | Phenyl Urethane Selectivity % Based On | |
|---|---|---|---|---|---|
| | | DPH | NB | DPH + NB | Ethanol |
| 15 | FeOCl (3.7) | 99 | 100 | 96 | 96 |
| 16 | $FeCl_3$ (3.6) | 99 | 100 | 90 | 90 |
| 17 | $FeCl_2 \times 4H_2O$ (5.5) | 99 | 100 | 82 | 97 |
| 18 | $VCl_3$ (1.9) | 99 | 100 | 92 | 94 |
| 19 | $CuCl_2$ (1.9) + $CeCl_3$ (1.5) | 98 | 37 | 70 | 97 |
| 20 | $-Fe_2O_3$ (2.5) + aniline . HCl (3.3) | 99 | 90 | 98 | 99.5 |
| 21 | $V_2O_5$ (2.5) + aniline . HCl (3.3) | 99 | 100 | 93 | 100 |
| 22 | $MoO_3$ (2.5) + aniline . HCl (3.3) | 98 | 100 | 100 | 94 |

EXAMPLE 23

250 g of the following mixture were introduced into a 0.7 liter autoclave: $2 \times 10^{-3}\%$ by weight of $PdCl_2$, 4% by weight of FeOCl, 14.8% by weight of a bis-urea of 2,4-diamino toluene and 2-amino-4-nitrotoluene and 81% by weight of ethanol. The nitro groups of the urea used are oxidizing agents for the oxycarbonylation of the urea function. 120 bar of carbon monoxide were forced in at room temperature. The mixture was allowed to react for two hours at 180° C. The bis-urea was converted quantitatively. The bis-urethane of 2,4-diisocyanatotoluene was obtained with a selectivity of 50 mol % in addition to 10 mol % of isomeric aminourethanes.

What is claimed is:

1. A process for the preparation of a urethane comprising reacting an N,N'-disubstituted area with an organic compound containing at least one hydroxyl group in the presence of carbon monoxide and molecular oxygen and a catalyst comprising:
   (a) a noble metal and/or a noble metal compound of the eighth subgroup of the periodic system of elements; and
   (b) a compound of an element of the third to fifth main group and/or first to eighth subgroup of the periodic system of elements other than the compounds of group (a) capable of undergoing Redox reactions under the reaction conditions.

2. The process of claim 1 wherein the reaction mixture includes an organic nitro compound.

3. The process of claim 2 wherein the N,N'-disubstituted urea is a symmetric N,N'-diaryl urea and the organic nitro compound is an aromatic nitro compound having the same aryl group as the urea.

4. A process for the preparation of a urethane comprising reacting a nitro-substituted N,N'-diaryl urea with an organic compound containing at least one hydroxyl group in the presence of carbon monoxide and molecular oxygen with a catalyst comprising:
   (a) a noble metal and/or a noble metal compound of the eighth subgroup of the periodic system of elements; and
   (b) a compound of an element of the third to fifth main group and/or first to eighth subgroup of the periodic system of elements other than the compounds of group (a) capable of undergoing Redox reactions under the reaction conditions.

5. The process of claim 1 or 4 wherein the catalyst component (a) is palladium, rhodium, palladium compounds and/or rhodium compounds.

6. The process of claim 4 wherein the catalyst compound (b) is an oxychloride of an element of the third to fifth main group or first to eighth subgroup of the periodic system.

7. The process of claim 4 wherein the catalyst component (b) is an oxide and/or hydroxide of an element of the third to fifth main group or first to eighth subgroup of the periodic system in combination with a compound containing chlorine bound anionically as chloride characterized in that the chlorine compound is capable of activating the oxide and/or hydroxide with formation of chloride.

8. The process of claim 4 wherein the catalyst compound (b) is iron oxychloride.

9. The process of claim 1 or 4 wherein the organic compounds having at least one hydroxyl group are monohydric primary aliphatic alcohols having from 1 to 6 carbon atoms.

10. The process of claim 1 or 4 wherein the reaction is carried out at a temperature of from 100° to 300° C. and a pressure of from 5 to 500 bars.

11. A process for the preparation of a urethane comprising reacting an N,N'-disubstituted urea with an organic compound containing at least one hydroxyl group in the presence of carbon monoxide and molecular oxygen and/or an organic nitro compound and a catalyst comprising:
   (a) a noble metal and/or a noble metal compound of the eighth subgroup of the periodic system of elements; and
   (b) an oxychloride of an element of the third to fifth main group or first to eighth subgroup of the periodic system.

12. The process of claim 11 wherein the catalyst component (b) is iron oxychloride.

13. A process for the preparation of a urethane comprising reacting an N,N'-disubstituted urea with an organic compound containing at least one hydroxyl group in the presence of carbon monoxide and molecular oxygen and/or an organic nitro compound and a catalyst comprising:
   (a) a noble metal and/or a noble metal compound of the eighth subgroup of the periodic system of elements; and
   (b) an oxide and/or hydroxide of an element of the third to fifth main group or first to eighth subgroup of the periodic system in combination with a compound containing chlorine bound anionically as chloride characterized in that the chlorine compound is capable of activating the oxide and/or hydroxide with formation of chloride.

* * * * *